US006257240B1

(12) United States Patent
Shesol

(10) Patent No.: US 6,257,240 B1
(45) Date of Patent: Jul. 10, 2001

(54) COMBINATION PROTECTIVE MEDICAL GUARD WITH SELF-CONTAINED SUPPORT

(75) Inventor: Barry F. Shesol, Aurora, CO (US)

(73) Assignee: Tapeless Technologies, Inc., Aurora, CO (US)

( * ) Notice: Subject to any disclaimer, the term of this patent is extended or adjusted under 35 U.S.C. 154(b) by 0 days.

(21) Appl. No.: 09/587,402

(22) Filed: Jun. 5, 2000

(51) Int. Cl.$^7$ .................................................. A61F 5/37
(52) U.S. Cl. .................. 128/877; 128/878; 128/879; 128/DIG. 6; 602/79
(58) Field of Search .................................. 128/877, 878, 128/879, DIG. 6; 602/79, 41, 53, 75; 606/213, 215, 216

(56) References Cited

U.S. PATENT DOCUMENTS

| 432,798 | * | 7/1890 | Hirst | 602/79 |
| 5,577,516 | * | 11/1996 | Schaeffer | 128/877 |
| 5,662,599 | * | 9/1997 | Reich | 602/79 |
| 5,891,078 | * | 4/1999 | Turngren | 602/58 |

* cited by examiner

*Primary Examiner*—Michael A. Brown
(74) *Attorney, Agent, or Firm*—Edwin H. Crabtree; Ramon L. Pizarro; Donald W. Margolis

(57) ABSTRACT

A combination medical protective guard and self-contained support for providing a painless access to a wound site, medical device or surgical site or protecting the site. The combination is adaptable for conforming to various parts of the anatomy of a human or an animal body and eliminates the use of adhesives. The support includes an elongated bidirectional wrap having hook fasteners at a first end for engaging a portion of a loop like material along a length of a second end of the wrap. The wrap allows for infinite adjustment along its length for either loosening or tightening the wrap when the site guard is received over the wound site or the infusion site. Also, the wrap may include a window opening with sides of the window opening received around a top portion of the protective guard. The window opening is used for viewing the site through the top of the protective guard. The guard is a dome-shaped housing having a base, a first end portion, a second end portion, a rounded top portion and a hollow interior. The hollow interior is used for receipt over the wound site or infusion site. The guard includes lines of weakness disposed on various locations thereon. The lines of weakness used for breaking through and forming one or more openings in the sides or in the top of the housing.

15 Claims, 1 Drawing Sheet

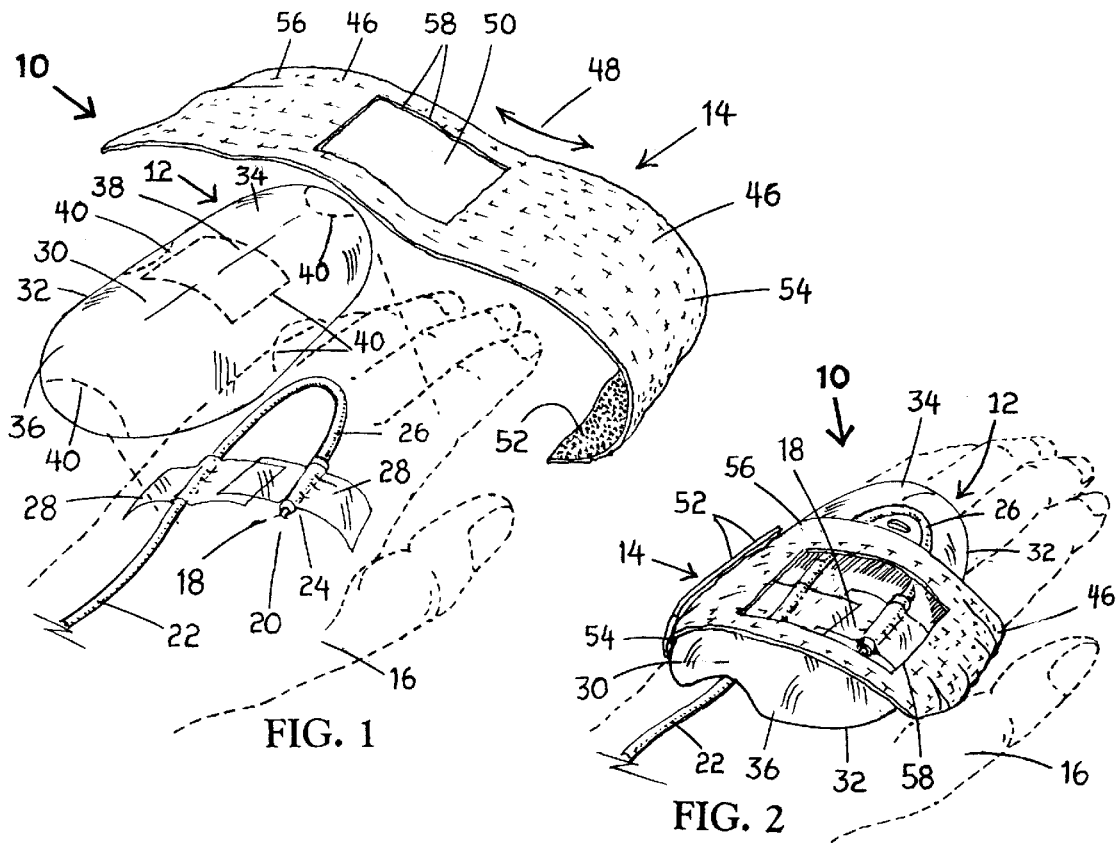
FIG. 1
FIG. 2
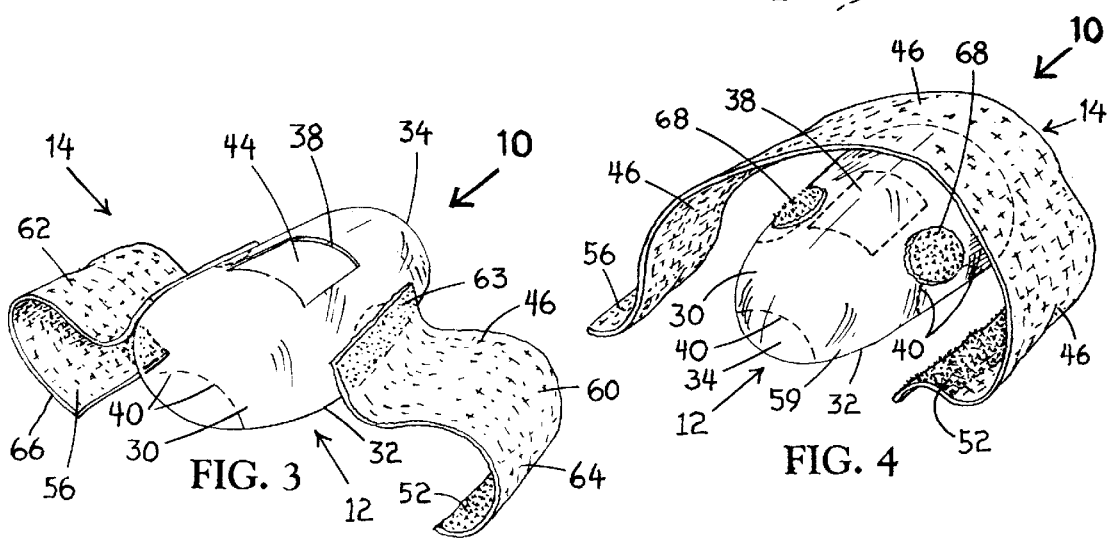
FIG. 3
FIG. 4
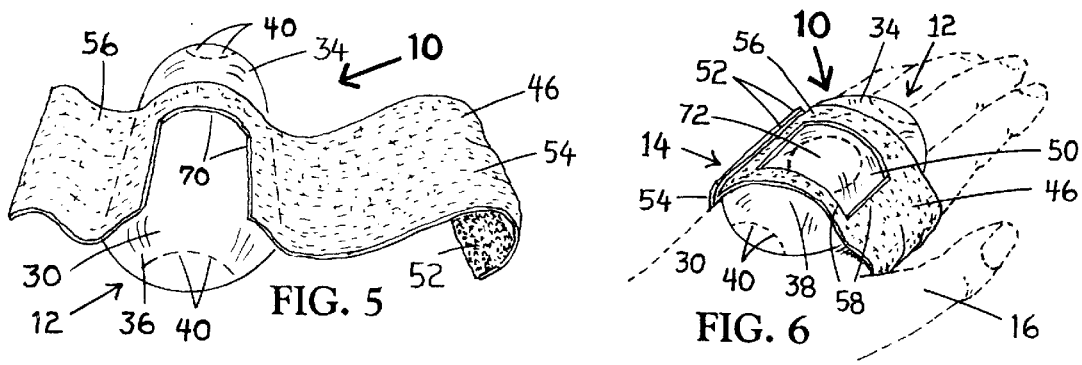
FIG. 5
FIG. 6

COMBINATION PROTECTIVE MEDICAL GUARD WITH SELF-CONTAINED SUPPORT

BACKGROUND OF THE INVENTION (a) Field of the Invention

This invention relates to medical, surgical and wound protective devices and more particularly, but not by way of limitation, to a combination protective medical guard with self-contained support. The combination having a bidirectional wrap attached to a variable configured dome-shaped housing received over a wound site, over a medical device or infusion site. The bidirectional wrap is used for securing the housing to various site locations on humans and animals.

(b) Discussion of Prior Art

Protective devices serve many purposes in medicine and are critical to the recovery of a patient. Different types of protective devices, some as simple as a plastic cup, help protect the transportation of medications within tubes, surgical drains, implants and vulnerable wound sites. At times, very unstable fractures, such as those of the face, require some protection, but as is obvious, casts cannot be used on the face. As a result, the protection and maintenance of these medical situations are the object of many techniques and devices used in an attempt to minimize the shortcomings of currently used applications. The subject invention addresses the following shortcomings of prior art protective devices, avoids the use or need for adhesives and tape and expands the application by means of a single device:

a. Difficulty with conforming to some anatomic locations, contours and particularly in areas of motion.

b. Adhesive allergies resulting in blisters, rashes, open wounds, scars and permanent pigmentation problems.

c. Inability to adhere in areas of raw tissue.

d. Lack of satisfactory adherence in hair-bearing areas.

e. Not reusable.

f. Pain associated with adhesive material removal.

g. Difficult to maintain in a combative patient or active child.

h. Has reduced effectiveness in moist environments.

i. Damaging in situations with adjacent injuries.

j. Complications from application are additive.

k. Tearing of the health care provider's gloves, resulting in loss of sterility with contamination or disruption of universal wound precautions.

The inventor of the subject patent application is a co-inventor of wound dressing support devices described in U.S. Pat. Nos. 5,456,660 and 5,662,599 to Shesol et al. These two patents disclose wound dressing support devices for holding a variety of standard wound dressings in place on top of an open wound and without the use of adhesives. Each device includes an elongated bidirectional wrap with a window opening therethrough. Also, this inventor is a co-inventor of an intravenous wound wrap described in U.S. Pat. No. 5,897,519 to Shesol et al. In U.S. Pat. No. 5,167,240 to Rozier et al., a plastic infusion site guard is described with a U-shaped base with open end. The infusion site guard is held on the patient using adhesive tape.

While the above mentioned patents describe individually an infusion site guard and the use of bidirectional wraps used to eliminate the use of adhesives, none of these patents individually or in combination teach or suggest the objects, benefits and the unique structure and features of using a stretchable bidirectional wrap for holding a protective guard in place, without the use of adhesive tape, above a wound site, a needle, a stoma, a catheter and other medical devices.

SUMMARY OF THE INVENTION

In view of the foregoing, it is a primary object of the present invention to provide a multifunctional protective guard and self-contained support which can be applied on various locations on the human body. Also, the combination protective guard and self-contained support can be used equally well for treating animals by a veterinarian. The various protected sites include peripheral, midline and central venous access sites, centrally implanted infusion ports, drains, tubes, implants, skin grafts, stoma and other vulnerable and fragile wound beds.

Another object of the invention is that the self-contained support is a bidirectional wrap, stretchable along its length, provided with hook fasteners at a first end of the wrap for engaging a portion of loop like material along the length of a second end of the wrap. The wrap allows for easy adjustment in either loosening or tightening the wrap when a protective medical guard is received over the wound site or device.

A further object of the combination is that in a single patient use scenario, it's lightweight, nonconstricting, reusable, washable, non-adhesive, disposable, versatile and able to be applied by the patient or with the help of a care giver.

Still another object of the invention is the wrap may be attached to the protective guard in a variety of ways to maximize the protective aspects of the invention.

In summary, the subject invention offers the following:

a. A reusable, lightweight and non-allergenic, latex-free protective guard.

b. Easy application and removal without the inherent problems of an adhesive.

c. Universal and functional in a variety of anatomic sites.

d. Usable for virtually any medical condition because of its variable configurations to fit different types of medical needs.

e. The protective guard may be transparent or opaque and includes various lines of weakness for breaking out portions of the guard for entrance and exiting of tubing and other medical devices and ventilation if required.

f. Preserves the integrity of local tissues.

g. Houses the entire site or medical device safely and in all directions affords protection by the nature of its closed housing configuration. The housing can be of various sizes and geometric shapes depending on the application.

h. Customizable to specific patient needs.

i. Application to human and animal clinical medical situations.

j. A closed or open environment compatible for wound healing.

k. A protective guard which does not apply pressure to the wound.

The invention includes a self-contained support made up of an elongated bidirectional wrap having hook fasteners at a first end for engaging a portion of a loop like material along a length of a second end of the wrap. The wrap allows for infinite adjustment along its length for either loosening or tightening the wrap when the protective guard is received over the area intended for protection. Also, the wrap may include a window opening with sides of the window opening received around a top portion of the protective guard. The window opening can be used for viewing the site through a hole made in the top of guard if desired for medical purposes.

Also, the invention includes a protective guard made up of a dome-shaped housing having a hollow interior. The hollow interior is used for receipt over the wound site. An end portion of the housing can be used for receipt over a portion of a supply tubing connected to a needle, a catheter or other infusion device by breaking out a portion of the protective housing.

These and other objects of the present invention will become apparent to those familiar with different types of wound dressings and wound wraps when reviewing the following detailed description, showing novel construction, combination, and elements as herein described, and more particularly defined by the claims, it being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 1 is a perspective view of the subject combination protective guard with self-contained support. The combination is disposed above a left hand of a patient. The protective guard includes a transparent or opaque dome-shaped housing along with portions of the housing having lines of weakness therein. The lines of weakness are used for breaking out portions of the housing. The support includes a bidirectional wrap with a window opening therein. The patient is shown with an intravenous needle inserted into a vein in the top of the hand. Also, one end of a supply tube is connected to the needle and looped on top of the hand as shown. A portion of one end of the housing has been broken out for the exiting of the supply tube.

FIG. 2 is another perspective view of the guard and self-contained support with the combination disposed above the infusion site on top of the hand. The support with bidirectional wrap is shown secured around the hand for holding the guard in place above the infusion site.

FIG. 3 is a perspective view of another embodiment of the combination with the bidirectional wrap divided into two separate wraps. One end of the two wraps is secured to opposite sides of the housing.

FIG. 4 is a perspective view of still another embodiment of the combination with the bidirectional wrap secured on a top portion of the housing using hook fasteners attached to opposite sides of the housing.

FIG. 5 is a perspective view of yet another embodiment of the combination with the bidirectional wrap having a "U" shaped opening therein with the side of the opening secured to the inside of the opposite sides of the housing.

FIG. 6 is a perspective view of the guard and self-contained support with the combination disposed above a skin graft site on top of the hand. The support with bidirectional wrap is shown secured around the hand for holding the protective guard in place above the skin graft site.

DESCRIPTION OF THE PREFERRED EMBODIMENTS

In FIG. 1, a perspective view of the subject combination protective medical guard with self-contained support is shown having a general reference numeral 10. The combination 10 broadly includes a multipurpose protective guard, having a general reference numeral 12, and a self-contained support, having a general reference numeral 14. The combination 10 is shown disposed above a left hand 16 of a patient. In this drawing, the top of the left hand 16 of the patient is shown with an infusion site 18 having an intravenous needle 20 inserted into a vein. Intravenous tubing 22 is shown with one end 24 attached to the needle 20 and an end portion 26 of the tube 22 formed in a loop as shown and secured to the top of the hand. This example is a standard method of applying and securing an intravenous needle for supplying intravenous fluid to the patient.

A small amount of adhesive tape 28 is shown in this drawing for holding an end of the needle 20 and the loop of the end portion 26 in place on top of the hand 16. Obviously, if the combination 10 was used to protect an open wound site, an implant, wound or stoma, no adhesives or adhesive tape would be required. As mentioned above, the subject invention is designed to eliminate the use of adhesives and in some applications to keep the use of tape to a minimum, as shown in this example.

While the infusion site 18 is shown in the drawings, it should be kept in mind that the subject invention can be used with various types of wound sites, body entrance sites or stoma and other medical applications, wherein a particular site on a human or an animal must be protected for a period of time to enhance the healing process.

The protective guard 12 is made up of a malleable dome-shaped housing 30. The housing may be transparent or opaque. Also, the housing 30, while shown in a dome-shape form, may come in various sizes and geometric shapes depending on the size of the wound site location, or object to be protected, the medical application, the anatomy on the patient's body and the size, age and type of patient being treated. Further, the height, length and width of the housing will vary depending on the particular medical need.

The housing 30, in this example, includes a base 32, which is designed to engage the patient's skin around the wound site or infusion site 18. Also, the housing includes a closed first end portion 34, a closed second end portion 36, a domed top portion 38 and a hollow interior. The hollow interior is used for receipt over the wound site or the infusion site 18. The first and second portions and the domed top portion all include lines of weakness, shown as dashed lines 40. By breaking out the lines of weakness 40, various shapes and sizes of openings can be formed in the housing 30. Also, one or more of the openings formed by the lines of weakness can be used for air and gas ventilation of the site 18.

While this particular configuration of the housing 30 is shown, various types, sizes and geometric shapes of transparent and opaque housings can be used equally well depending on the medical application and site location on the body.

The self-contained support 14 includes a bidirectional wrap 46 made of loose weave material and stretchable laterally along its length as indicated by arrow 48 with a window opening 50 therein. The wrap 46 includes hook fasteners 52 attached at a first end 54 of the wrap for releasably engaging a portion of the loose weave material along a length of a second end 56 of the wrap. The wrap 46 allows for infinite adjustment along its length for either loosening or tightening the wrap 46 when the site guard 12 is received over the wound site or the infusion site 18.

The window opening 50 with opening sides 58 are received above the rounded top portion 38 of the housing 30. The window opening 50, in this example, is used for viewing the site 18 through the transparent site guard 12 or a break out portion of the lines of weakness 40 shown in the top portion 38. Also, it can be appreciated that if there is no medical reason for viewing the site 18, the wrap 46 can be used without a window opening for securing the housing 30 in place.

In FIG. 2, another perspective view of the site guard 12 and the support 14 is shown with the combination 10 disposed above the site 18 on top of the hand 16. The support 14 is shown with the bidirectional wrap 46 secured around the hand for holding the dome-shaped housing 30 in place above the site 18. In this drawing, the first end 54 has been wrapped under the hand 16, with the hook fasteners 52 releasably engaging the loose weave material on the second end 56 of the wrap 46. As mentioned above, through the use of the hook fasteners 52 and the loose weave material of the wrap 46, infinite adjustments can be made along the length of the second end 56 for either tightening or loosening the wrap and holding the housing 30 in place above the site 18. It should be noted in this drawing, the lines of weakness 40 have been used to remove a portion of the closed second end portion 36 so that the tubing 22 can exit the protective guard 12.

While the engagement of the hook fasteners 52 with the loose weave material of the wrap 46 is discussed herein, it should be kept in mind that the second end 56 could include loop fasteners for releasably engaging the hook fasteners 52. Also, while the use of hook fasteners for engaging the loose weave material of the wrap 46 is a primary way of securing the protective housing above the wound site or infusion site, it can be appreciated by those skilled in the art that various types of releasable fasteners can be used for securing the first end of the wrap to the second end of the wrap without departing from the spirit and scope of the subject invention.

In FIG. 3, a perspective view of another embodiment of the combination 10 is shown with the bidirectional wrap 46 divided into first wrap portion 60 and a second wrap portion 62. One end 63 of the two wraps 60 and 62 is secured, using ultrasonic bonding, an adhesive and the like, to the first and second side portions 40 and 42 of the transparent housing 30. An opposite end 64 of the first wrap portion 60 includes hook fasteners 52. The hook fasteners 52 are used for releasably engaging the loose weave material on an opposite end 66 of the second wrap portion 62. In this embodiment and since the wraps 60 and 62 do not cover the rounded top portion 38, a hole 44, broken out using the lines of weakness 44 in the top portion 38, is used for viewing the site 18.

In FIG. 4, a perspective view of still another embodiment of the combination 10 is illustrated. In this drawing, the bidirectional wrap 46 is releasably secured to a pair of hook fastener 68 mounted on the sides of the housing 30. In this example, the loose weave material of the wrap 46 is used to releasable engage the hook fasteners 68 for holding the wrap on top of the housing. Also, in this arrangement, the wrap 46 can be attached anywhere along its length to the hook fasteners 68. This feature allows for ease in applying the combination 10 to various locations on the patient's body. Further, in this embodiment, the wrap 46 is used in conjunction with the housing 30, but does not include a window opening 50. If desired, the wrap 46 could include a window opening 50 for inspecting the site 18 similar to what is shown in FIGS. 1 and 2.

In FIG. 5, a perspective view of yet another embodiment of the combination 10 is shown. In this example, the bidirectional wrap 46 is shown having a "U" shaped opening 70 therein. Sides of the opening 70 are secured using ultrasonic bonding or an adhesive to the inside of the first and second side portions 40 and 42 of the dome-shaped housing 30.

In FIG. 6, a perspective view of the protective guard 12 and self-contained support 14 is illustrated. In this drawing, the combination 10 is shown disposed above a skin graft site 72 on top of the hand 16. The support 14 with bidirectional wrap 46 and window opening 50 is shown secured around the hand 16 for holding the site guard 12 in place above the skin graft site 72. In this embodiment of the housing 30, the housing completely covers the skin graft site 72 to prevent any contamination from an outside source.

While the above drawings illustrate a number of ways of using the bidirectional wrap 46 for holding the housing 30 above and around the infusion site 18, it can be appreciated there can be any number of ways of using the wrap 46 in conjunction with the housing 30 for protecting various wound sites and infusion sites.

Also, while the invention has been particularly shown, described and illustrated in detail with reference to the preferred embodiments and modifications thereof, it should be understood by those skilled in the art that changes in form and detail may be made therein without departing from spirit and scope of the invention as claimed, except as precluded by the prior art.

The embodiments of the invention for which an exclusive privilege and property right is claimed are defined as follows:

1. A combination protective medical guard with a self-contained support, the combination providing painless access to a wound site, an infusion site, a medical device and protecting the site, the site on a human or animal patient, the combination comprising:

an elongated bidirectional wrap having a first end and a second end;

first fastener means attached to the first end of said wrap, said first fastener means for releasably engaging the second end of said wrap and securing said wrap on the patient; and a housing having a hollow interior, said housing adapted for receipt over and around the wound site or the infusion site, said housing including a base, a first end portion, a second end portion and a top portion, said housing having a plurality of lines of weakness therein, said lines of weakness used for breaking through said housing and forming at least one hole therein, said bidirectional wrap engaging a portion of said housing for holding said housing on the patient.

2. The combination as described in claim 1 wherein said wrap is made of loop like material and wherein said first fastener means is hook fasteners, said hook fasteners attached to the first end of said wrap, said hook fasteners for engaging a portion of the loop like material along a length of the second end of said wrap.

3. The combination as described in claim 1 wherein said wrap includes a window opening therein, sides of said window opening received around a top portion of said housing.

4. The combination as described in claim 1 further including a second fastener means attached to a portion of said housing, said second fastener means for releasably engaging a portion of said wrap.

5. A combination protective medical guard with a self-contained support, the combination providing painless access to a wound site, an infusion site, a medical device and protecting the site, the site on a human or animal patient, the combination comprising:

an elongated bidirectional wrap made of loose weave material, said wrap having a first end and a second end;

hook fasteners attached to the first end of said wrap, said hook fasteners for releasably engaging the loose weave material along a length of the second end of said wrap and securing said wrap on the patient; and a housing having a hollow interior, said housing adapted for receipt over and around the site, said housing including a base, a first end portion, a second end portion, sides and a top portion, said housing having a plurality of lines of weakness therein, said lines of weakness used for breaking through said housing and forming at least one hole therein; said bidirectional wrap engaging a portion of said housing for holding said housing on the patient.

6. The combination as described in claim 5 wherein said wrap includes a window opening therein, sides of said window opening received around a top portion of said housing, said window opening and said housing providing viewing of the wound site or the infusion site.

7. The combination as described in claim 5 further including a second fastener means attached to a portion of said housing, said second fastener means for releasably engaging a portion of said wrap and holding said wrap on top of said housing.

8. The combination as described in claim 5 wherein said housing has is made of a transparent material.

9. The combination as described in claim 5 wherein said housing has is made of an opaque material.

10. A combination protective medical guard with a self-contained support, the combination providing painless access to a wound site, an infusion site, a medical device and protecting the site, the site on a human or animal patient, the combination comprising:

an elongated bidirectional wrap made of loose weave material, said wrap having a first end and a second end;

hook fasteners attached to the first end of said wrap, said hook fasteners for releasably engaging the loose weave material along a length of the second end of said wrap and securing said wrap on the patient; and a variably configured dome-shaped housing having a hollow interior, said housing adapted for receipt over and around the wound site or the infusion site, said housing including a base, a first end portion, an second end portion, sides and a top portion, said housing having a plurality of lines of weakness in the first and second end portions, the sides and the top portion, said lines of weakness used for breaking through said housing and forming at least one hole in said housing, said bidirectional wrap secured to a portion of said housing for holding said housing on the patient.

11. The combination as described in claim 10 further including a hook fasteners attached to a portion of said housing, said hook fasteners for releaseably engaging a portion of said wrap and holding said wrap on top of said housing.

12. The combination as described in claim 10 wherein said wrap is secured to said housing using heat bonding.

13. The combination as described in claim 10 wherein said wrap is divided into a first wrap portion and a second wrap portion, one end of said first and second wrap portions attached to said housing, an opposite end of the first wrap portion having said hook fasteners mounted thereon.

14. The combination as described in claim 10 wherein said wrap includes a window opening therein, sides of said window opening received around a top portion of said housing, said window opening and said housing providing viewing of the wound site or the infusion site.

15. The combination as described in claim 10 wherein said housing includes a base, a closed first end portion, an closed second end portion, a rounded top portion and downwardly curved sides, the base adapted for engaging the skin of the patient and around the wound site or infusion site.

* * * * *